United States Patent [19]

Murtfeldt

[11] Patent Number: 4,592,920
[45] Date of Patent: Jun. 3, 1986

[54] METHOD FOR THE PRODUCTION OF AN ANTIMICROBIAL CATHETER

[75] Inventor: Robert L. Murtfeldt, Redondo Beach, Calif.

[73] Assignee: Baxter Travenol Laboratories, Inc., Deerfield, Ill.

[21] Appl. No.: 496,367

[22] Filed: May 20, 1983

[51] Int. Cl.⁴ .................... B05D 3/02; A01N 1/02; A61M 5/325; A61M 25/00
[52] U.S. Cl. .................................. 427/2; 427/387; 427/393.5; 604/265; 604/280
[58] Field of Search ............... 604/265, 280; 427/2, 427/387, 393.5

[56] References Cited

U.S. PATENT DOCUMENTS 3,695,921 10/1972 Shepherd et al. ............. 604/280 X
4,054,139 10/1977 Crossley .......................... 604/265

FOREIGN PATENT DOCUMENTS 3228849 2/1984 Fed. Rep. of Germany ...... 604/256

Primary Examiner—Michael R. Lusignan
Attorney, Agent, or Firm—Roger A. Williams

[57] ABSTRACT

A method for the production of antimicrobial catheters includes the steps of comminuting an antimicrobial metal compound to a particle size of up to about 30 microns in diameter. The comminuted antimicrobial metal compound is suspended in a suspending agent which can be cured to form a catheter or which can be formed to provide a coating on a previously formed catheter. The suspending agent is coated to either form the catheter or to form a coating on a catheter. Upon curing of the suspending agent, an outer surface is formed on the catheter, which outer surface includes the antimicrobial metal compound, thereby imparting antimicrobial activity to the catheter.

38 Claims, No Drawings

METHOD FOR THE PRODUCTION OF AN ANTIMICROBIAL CATHETER

BACKGROUND OF THE INVENTION

The invention herein is directed to a catheter which can be used in the treatment and prevention of nosocomial infection frequently encountered in long term catherization. One theory proposed for the incidence and transmission of infection to a catheterized patient is the migration of microbes from the surrounding environment into the patient's system along the route of the catheter. One of the more common nosocomial infections occurs with urinary catheterization of hospitalized patients. With the conversion from open to closed urinary drainage systems, there has been a diminishing of nosocomial infections but still over 20% of patients with indwelling catheters exhibit sympton of urinary tract infections.

With such a high incidence of infection and a large number of patients catheterized each year, there is a great concern in the hospital staff in following good practices of catheter care so as to minimize the likelihood of bacterial transfer. In a catheterized patient, there is a strong likelihood that the patient may be cross-contaminated. That is, the patient is generally located in a room with a similarly situated patient and the catheter and collection bags must be monitored and emptied at frequent intervals, thus increasing the likelihood of cross-contamination between patients. It is difficult to maintain collected urine and to remove collected urine in a sterile condition or utilizing a totally sterile procedure. It would, therefore, be desirable to provide a catheter which could be used in association with a closed catheter system, which catheter can prevent or inhibit the migration of microbes from the surrounding environment of the patient into the patient.

SUMMARY OF THE INVENTION

The invention herein is directed to a catheter which exhibits antimicrobial activity and which, therefore, inhibits or prevents the migration of microbes along the catheter. The invention herein is more appropriately directed to a method for forming such an antimicrobial catheter. In particular, the method includes the steps of comminuting an antimicrobial metal compound to a particle size of up to about 30 microns in diameter. The antimicrobial metal compound is comminuted in preparation of suspending the comminuted antimicrobial metal compound in a suspending agent. A preferred antimicrobial metal compound is silver oxide which can be readily comminuted to the desired particle sizes of up to 30 microns and preferably within a range of particle sizes of up to 5 microns.

The comminuted antimicrobial metal compound is suspended in a suspending agent which is capable of being cured to form at least a portion of a catheter. The suspending agent can be the material of the catheter itself or can be another material which can be coated onto the catheter to form a layer on the surface of the catheter, which layer contains the antimicrobial metal compound. Catheters which can be used herein included latex and silicone catheters. Suitable suspending agents include silicone, polyurethanes and tetrafluoroethylenes.

The comminuted antimicrobial metal compound is suspended in the suspending agent and the suspending agent is then cured to form a catheter or a catheter is coated with the suspending agent and subsequently cured to form the catheter herein.

When the suspending agent is coated on a catheter, it can be desirable to pretreat the catheter to prepare the surface for accomodating the coating of suspending agent. The surface of the catheter can be pretreated by leaching from the catheter any undesirable compounds which may interfere with the coating or bonding of the suspending agent to the catheter. Another step which can be performed to pretreat the surface of the catheter can be the coating of the surface of the catheter with a bridging compound which has an affinity for both the material of the catheter and the suspending agent. The use of such a bridging compound can provide for bonding of the coating of suspending agent to the catheter surface.

DETAILED DESCRIPTION

The method herein and the resulting catheter have utility in reducing the risk of acquiring a nosocomial infection encountered by a patient with an indwelling catheter. The use of a catheter formed by the method herein can reduce the catheter care and aseptic regimen currently required to be perfomed by the attendant of a catheterized patient. The catheter herein itself provides an antimicrobial activity which prevents or inhibits the migration of microbes such as bacteria toward the patient along the catheter, either on the outer surface or on the inner surface. Although the invention can be practiced on catheters for use in many procedures; i.e., urinary catheters, IV catheters, wound drains, and the like, for ease of description the invention will be described with regard to urinary catheters. A urinary catheter formed by the method herein provides a catheter which is useful in preventing nosocomial infections, regardless of the care provided during the measuring or emptying of a urinary drainage bag connected to the catheter, because any bacterial which migrates from the bag along the catheter encounters the antimicrobial metal compound and such bacterial migration is substantially prevented or inhibited.

The antimicrobial activity of the indwelling catheter is provided by an antimicrobial metal compound which is fixed to the catheter in at least an outer layer on the catheter. That is, the antimicrobial metal compound is imbedded with the catheter such that it is imbedded along the inner drainage surface and/or the outer surface of the catheter so as to contact any microbes which may attempt to migrate along the catheter. It has been found herein that the antimicrobial metal compound can be used most efficiently by providing the antimicrobial metal compound in a coating on the surface of the catheter. By utilizing a coating on the surface of the catheter, less antimicrobial metal compound is required and the antimicrobial metal compound is placed in an optimum position for encountering or contacting any microbes that attempt to migrate along the catheter. Although described herein primarily with regard to providing a coating on the catheter, the antimicrobial metal compound can be imbedded within the entire catheter. However, such a construction is less desirable as antimicrobial metal compound imbedded within the sidewall of the catheter has less likelihood of encountering any migrating microbes. In addition, since the antimicrobial metal compound can be expensive, it is desirable to decrease the cost of antimicrobial metal compound by utilizing a coating or layering of the antimicrobial metal compound along the surface of the catheter.

The antimicrobial catheter herein is best described with regard to the method of its manufacture. Any catheter can be formed so as to have antimicrobial activity by the method herein. That is, regardless of the end use of the catheter, it can be provided with antimicrobial activity. For example, urological, IV, cardiac care, wound drainage, hydrocephalus and the like catheters can be given antimicrobial activity by the method herein. The antimicrobial activity can be imparted at the time of forming the catheter or subsequently by coating a catheter which has already been formed. In addition, various compositions of matter which are used to form a catheter can be used while still enabling the ability to provide an antimicrobial activity. The invention herein will be primarily described with regard to latex and silicone catheters.

To prepare the antimicrobial catheter herein, an antimicrobial metal compound is selected which exhibits antimicrobial activity. Many metals exhibit antimicrobial activity. However, only those antimicrobial metal compounds which are biocompatible with the body are suitable for the practice of the invention herein. Examples of acceptable antimicrobial metals include silver, gold and copper. The antimicrobial metal is preferably used in a solid state. Thus, any compound or composition of the antimicrobial metal which provides a solid material can be utilized in the practice of the method herein. For example, with regard to the previously mentioned specific examples of antimicrobial metals, specific compounds of these metals include silver oxide, gold thiogylcolate and copper oxide.

The solid antimicrobial metal compound is comminuted to provide a particle size of up to about 30 microns in diameter. A preferred particle size of the comminuted antimicrobial metal compound is up to about 5 microns in diameter. Such a range and preferred range of particle sizes provides a homogenous suspension of the antimicrobial metal compound when it is suspended in a suspending agent in a subsequent step of the method. The antimicrobial metal compound can be comminuted using any available technique for crushing or micronizing the solid particles to the desired size. Many of such techniques are known to those skilled in the art.

The comminuted antimicrobial metal compound is added to a suspending agent, which suspending agent is capable of being cured to form a catheter or at least a portion of a catheter. For example, for a latex catheter the suspending agent can be latex, silicone, polyurethane, or tetrafluoroethylene. For a silicone catheter, the suspending agent can be silicone, polyurethane or tetrafluoroethylene. Each of the suspending agents can be cured to form a catheter or can be coated onto an existing catheter and cured to form at least a portion; i.e., a coating or layer on the catheter.

A suspending agent is selected which is compatible with the composition of the catheter. That is, a suspending agent which can bond to the catheter upon curing or which will adhere to the catheter upon curing. The bonding or adherence to the catheter can be through another agent such as a bridging or linking compound which as an affinity for both the suspending agent and the material of the catheter. Such a bridging compound will be discussed hereinafter.

It has been found herein that for a latex catheter, it is preferable to coat the latex catheter with a curable suspending agent containing the antimicrobial metal compound. The preferred suspending agent for such a coating procedure is a room temperature vulcanizable (RTV) silicone. An especially preferred silicone suspending agent is available from Dow Corning as Catalog No. Q7-2630 which when combined with a solvent (Catalog No. Q7-2650) and a catalyst (Catalog No. Q7-2640) for the curing provides an acceptable suspending agent. Upon curing the silicone suspending agent, there is cross-linking between acetoxy groups of the polymeric chains.

The comminuted antimicrobial metal compound is thoroughly mixed with the suspending agent to form a suspension which can be a dipping suspension into which a catheter can be dipped to provide a coating of the suspending agent and antimicrobial metal compound on the surface of the catheter. In those situations wherein the suspending agent forms the catheter itself, again a dipping suspension can be formed into which catheter forms can be immersed for coating the forms with the suspending agent containing the antimicrobial metal compound. Upon curing the suspending agent coated catheter or form, there is formed a catheter having its surface or surfaces covered by the suspending agent containing the antimicrobial metal compound. That is, when a form is dipped into the suspending agent it is coated with the suspending agent containing the antimicrobial metal compound and when the form is subsequently removed, the lumen of the catheter exhibits antimicrobial activity because of the presence of the antimicrobial metal compound which forms the entire catheter. When a catheter is dipped into the suspending agent containing the antimicrobial metal compound, the catheter is dipped into the suspension with its funnel end immersed in the dipping suspension. In this procedure, the suspending agent containing the antimicrobial metal compound can coat the inner and outer surfaces of the catheter. That is, the lumen of the catheter can be coated with an antimicrobial coating. In some instances, the lumen is sufficiently small in diameter and the inner surface is not coated in any substantial amount. It is desirable to have both the outer and inner surfaces of the catheter coated with an antimicrobial layer as migration of microbes along either the outer or inner surface can be prevented or inhibited. However, for urinary catheters used in closed drainage systems, it is desirable to coat only the outer surfaces of the catheter as bacterial migration along the lumen is generally effectively prevented by the closed system or drip chambers in the system. Migration along the outside of the catheter does present an avenue for nosocomial infection and a coating on such outer surface is, therefore, desirable.

In the step of coating a catheter with a layer of suspending agent containing the antimicrobial metal compound, it is preferable to coat the catheter with a coating having a thickness of from about 1 to about 15 microns. In the preferred embodiment coating a latex catheter using a silver oxide antimicrobial metal compound, the coating on the catheter contains from about 0.2 milligrams to about 50 milligrams of silver.

After the catheter form or catheter is dipped into the suspending agent containing the antimicrobial metal compound, the suspending agent is cured to adhere the suspending agent to the catheter or to form the catheter. The curing of the suspending agent causes the suspending agent to polymerize and form a resilient coating on the catheter. The presence of the antimicrobial metal compound in the coating provides an antimicrobial activity to the coating. As the coating is generally about 1 to about 15 microns thick, there is a substantial presence of the antimicrobial metal compound near the surface of the coating such than an antimicrobial activity is imparted to the coating and thereby the catheter.

When the method herein is practiced to provide a layered coating of the antimicrobial metal compound on the surface of a catheter, it is desirable to prepare the surface of the catheter before the coating step. The preparation of the surface of the catheter can include a leaching step wherein undesirable compounds present in the catheter can be removed by solvent leaching. The preparation of the surface can also include coating the surface with a bridging compound which exhibits an affinity for both the material of the catheter and the material of the suspending agent.

The surface of the catheter can be leached by immersing or dipping the catheter into a leaching solvent. During the formation of the catheter, there can be present in the catheter composition some compounds which could affect the bonding of the suspending agent to the catheter or the subsequent curing of the suspending agent. In addition, some compounds can be present which could interact with the antimicrobial metal compound. Therefore, it is desirable to pretreat the catheter to be coated by solvent leaching. Such a solvent leaching step can leach antioxidants, catalysts and other compounds which can be present in the catheter due to the process of forming the catheter. When the catheter is a latex catheter, it has been found that a preferred leaching solution includes a ternary azeotropic mixture of toluene, isopropyl alcohol and water. Such a leaching solution is capable of removing antioxidants and catalysts which can remain in the latex catheter and which are initially present in the latex dipping solution during the step of forming the catheter. The leaching solution can be thoroughly rinsed from the catheter and the catheter permitted to dry to remove any excess leaching solution prior to coating.

Following the leaching step, the surface can be further prepared by coating the catheter surface with a bridging compound such as silicone primer. The bridging compound can act as a bridging agent for the suspending agent and catheter to bind the suspending agent to the catheter through a chemical bond. For a latex catheter and a silicone suspending agent, the preferred briding compound has been found to be mercaptopropyl trimethoxysilane. Such a compound has a mercapto moiety which has an affinity for latex and a silane moiety which has an affinity for silicone. The mercaptopropyl trimethoxysilane can be dissolved in a suitable solvent such as acetone and isopropyl alcohol and coated on the latex catheter. A suitable peroxide catalyst such as vulcup R, commercially available from Hercules, Inc., can be used to initiate the bonding of the mercaptopropyl trimethoxysilane to the latex catheter. The catheter can be dipped into the solution of the mercaptopropyl trimethoxysilane and coated with the bridging compound. The coated catheter is air dried for about 15 minutes to 3 hours to provide bonding of the bridging compound to the catheter.

Following coating the catheter with the bridging compound, the catheter can be dipped or immersed into the suspending agent containing the antimicrobial metal compound. The catheter is dipped into the suspending agent, then upon its removal it is permitted to dry for approximately one hour. Following drying of the catheter, the catheter coated with the suspending agent is cured to cure the suspending agent and form a coating of the suspending agent containing the antimicrobial metal compound. For the latex catheter and silicone suspending agent, the curing generally can be accomplished at 23° Centigrade and 50% relative humidity for approximately 5 days. Increasing the temperature can correspondingly reduce the curing time. The coating provided on the catheter is generally about 1 micron to 0.06 inches thick and contain from about 0.2 milligrams to about 50 milligrams of the antimicrobial metal compound per catheter.

In addition to providing the step of applying a bridging compound to the catheter, an additional step of providing a silicone coating to the bridging compound prior to applying the suspending agent coating can be performed. By providing such a thin coating to the bridging compound, the bridging compound is able to react with the carrying material; i.e., the suspending agent, to provide a strong adhesion. Then, when the suspending agent containing the antimicrobial metal compound is coated over the thin coating of suspending agent, there is good adhesion upon curing due to the identity of the suspending agent in the thin coating and in the suspending agent coating containing the antimicrobial metal.

The antimicrobial metal compound is substantially fixed in the cured suspending agent. That is, the antimicrobial metal compound is generally not leachable from the coating, especially with regard to being leached by the action of biological fluids.

In addition to the steps of preparing the surface of the catheter to be coated with the suspending agent containing the antimicrobial metal compound, there can be employed a step of post-treating the coating of the suspending agent containing the antimicrobial metal compound after it has been applied to the catheter. For example, a thin layer of the suspending agent can be dissolved from the coating to expose additional antimicrobial metal compound. By exposing additional antimicrobial metal compound, there is made available additional metal compound to interact with microbes which may migrate along the catheter, thus increasing the antimicrobial activity of the catheter. As can be seen in the table herein, a potassium hydroxide treatment of the coating can be employed when the coating is a silicone coating containing the antimicrobial metal compound. The potassium hydroxide dissolves an outer layer of the silicone, thereby exposing additional antimicrobial metal compound. In addition to using a potassium hydroxide treatment of the coating, other surface treatments can include the use of a 30% hydrogen peroxide solution which can be used in times up to about 30 minutes and a 100% methyl ethyl ketone treatment which can be used in times up to about 15 minutes. Such treatments, as with the potassium hydroxide treatment, dissolve an outer layer of the silicone, thereby exposing additional antimicrobial metal compound upon the surface of the catheter.

The antimicrobial activity of the catheter formed by the method herein was demonstrated through in vitro testing. The antimicrobial activity of the silver coated catheter was shown in tests using *Escherichia coli ATCC* 9980 and *Staphylococcus Aureus ATCC* #10390. Two tubes of 4 to 5 milliliters were spun down. The resultant pellants were resuspended for each strain in 10 milliliters of phosphate buffer. The resultant solution was diluted 1 to 10 for the respective bacteria to be used as an inoculum. The approximate count in each inoculum solution was about 10$^7$ organism per milliliter. To determine the initial count of organisms, each of the inoculums was plated out using conventional plating techniques.

Each of the catheters that was tested was first sterilized using ethylene oxide gas, then cut to provide separate sections each approximately one-half inch in length. The two sections were tested in a phosphate buffer solution. Two catheter sections were placed inside a petri dish and secured in the petri dish using a small drop of stopcock grease. The petri dishes were inoculated with the inoculum in an amount containing $5 \times 10^4$ to $5 \times 10^5$ total bacteria using a micropipettor to apply three drops of approximately 10 microliters total volume to the top surface of each catheter. The petri dishes containing the inoculated catheter sections were then incubated at 37° Centigrade in a water bath for 60 minutes. The petri dishes were removed from the water bath and the catheter sections carefully removed. The catheter sections were placed into a phosphate buffer blank and shaken. Dilutions of the resulting solution were plated out in dilutions of $10^0$ through to $10^{-5}$. Plates were poured with agar utilizing conventional techniques. The plates were incubated at 37° Centigrade for 24 to 48 hours. The plates were then evaluated for bacterial count. The results of the tests are given in the following table.

against bacterial growth as the bacterial counts were reduced from 10$^5$ to less than 10. It can be seen from the above table that a subsequent potassium hydroxide treatment of the coating containing the antimicrobial metal is useful when that coating is a silicone coating. The alkaline treatment is believed to remove a top layer of silicone from the coating, thereby allowing additional silver oxide to become available for interaction with inoculum.

As can be recognized from the description herein, the method herein of providing an antimicrobial surface to a catheter can also have application to providing an antimicrobial surface to a substrate which may be a device other than a catheter. For example, body implantable medical devices can be provided with an antimicrobial coating by the method described herein. Such implantable devices would then exhibit antimicrobial activity. The method herein is especially useful in preparing medical devices which can be partially inserted in the body while leaving a portion extending from the body. In such devices, a bacterial pathway is created into the body along the surface of the device. Using the method herein to provide an antimicrobial surface to the device prevents or inhibits microbial migration along such a surface. The use of antimicrobial metals is especially desired for coating such devices as such antimicrobial metals generally provide a broad spectrum antimicrobial activity against both gram positive and

| | | IN VITRO ANTIMICROBIAL EVALUATION OF SILVER COATED CATHETER | | | | | | | |
|---|---|---|---|---|---|---|---|---|---|
| | Samples | Number of Bacteria Recovered/Catheter Section | | | | | | | |
| | (All Samples Contain | *Escherichia coli* | | | | *Staphylococcus Aureaus* | | | |
| Exp. | 3% Solids and 0.25% Fluorad Treated) | 9% Ag$_2$O | 7.5% Ag$_2$O | 6% Ag$_2$O | 4.5% Ag$_2$O | 9% Ag$_2$O | 7.5% Ag$_2$O | 6% Ag$_2$O | 4.5% Ag$_2$O |
| 1 | 10% KOH - 5 min. 37 sec. | <10, <10 | <10, <10 | <10, <10 | <10, <10 | <10, <10 | <10, <10 | <10, <10 | <10, <10 |
| 2 | 10% KOH - 2 min. 49 sec. | <10, <10 | <10, <10 | <10, <10 | <10, <10 | <10, <10 | <10, <10 | <10, <10 | <10, <10 |
| 3 | 10% KOH - 5 min. 37 sec. 5% Sodium Phosphate Acid Washed | <10, <10 | <10, <10 | <10, <10 | <10, <10 | <10, <10 | <10, <10 | <10, <10 | <10, <10 |
| 4 | 10% KOH - 2 min. 49 sec. 5% Sodium Phosphate Acid Washed | <10, <10 | <10, <10 | <10, <10 | <10, <10 | <10, <10 | <10, <10 | <10, <10 | <10, <10 |
| | Initial inoculum | | $2.1 \times 10^5$ | | | | $1.4 \times 10^5$ | | |
| | Negative Control (0 % Ag$_2$O) | | $1.3 \times 10^5$ | | | | $1.0 \times 10^5$ | | |

The above table illustrates the results of four experiments wherein a latex catheter coated by the method herein was formed and subsequently tested for antimicrobial activity by the above described procedure. In each of the experiments the latex catheter was coated with a coating solution containing 3% silicone solids and comminuted silver oxide in amounts by weight of 9%, 7.5%, 6% and 4.5% when evaluated against *Escherichia coli* and 9%, 7.5%, 6% and 4.5% when evaluated against *Staphylococcus Aureus*. Two sections of each catheter was tested. After coating each of the latex catheters with the silver oxide in silicone coating, the catheters wer treated with the 10% potassium hydroxide solutions for the times indicated. In experiments 3 and 4, the catheters were rinsed with a 5% sodium phosphate acid wash to remove remaining potassium hydroxide solution from the surface.

As can be readily seen from the table, the catheter coated with a coating containing an antimicrobial metal compound does provide inhibition and/or prevention gram negative bacteria. The method herein is especially useful in manufacturing urinary catheters. By providing a coating on at least the outer surface of such a catheter, migration of bacteria which may be present in the environment surrounding the patient along the outer surface of the catheter is substantially prevented or inhibited. By combining the antimicrobial catheter with a closed urinary drainage system, a total urinary drainage system for preventing noscomial infection can be obtained. In view of the large incidence of noscomial infections encountered by patients with long term indwelling urinary tract catheters, the system fulfills a long felt need.

I claim:

1. A method for the production of an antimicrobial catheter, the method comprising the steps of:
   selecting a catheter from the group consisting of silicone catheters and latex catheters to be coated with an antimicrobial coating;

comminuting an antimicrobial metal compound to a particle size of up to about 30 microns in diameter;

suspending the comminuted antimicrobial metal compound in a curable suspending agent capable of bonding to the surface of the catheter;

coating the catheter with the suspending agent containing suspended antimicrobial metal compound; and curing the suspending agent to bond the suspending agent containing antimicrobial metal compound to the surface of the catheter and to form an antimicrobial catheter.

2. A method as recited in claim 1 wherein the suspending step comprises suspending the antimicrobial metal compound in a curable suspending agent selected from the group consisting of silicone, polyurethane and tetrafluoroethylene.

3. A method as recited in claim 1 wherein the antimicrobial metal compound is selected from compounds of silver, gold and copper.

4. A method as recited in claim 3 wherein the antimicrobial metal compound comprises silver oxide.

5. A method as recited in claim 3 wherein the antimicrobial metal compound comprises gold thioglycolate.

6. A method as recited in claim 1 wherein the catheter comprises a latex natural rubber catheter.

7. A method as recited in claim 6 wherein the suspending agent is selected from the group consisting of silicone, polyurethane and tetrafluoroethylene.

8. A method as recited in claim 7 wherein the suspending agent comprises silicone.

9. A method as recited in claim 8 wherein the antimicrobial metal compound comprises silver oxide.

10. A method as recited in claim 1 wherein the catheter comprises a silicone catheter.

11. A method as recited in claim 10 wherein the suspending agent is selected from the group consisting of silicone, polyurethane and tetrafluoroethylene.

12. A method as recited in claim 11 wherein the suspending agent comprises silicone.

13. A method as recited in claim 12 wherein the antimicrobial metal compound comprises silver oxide.

14. A method for the production of an antimicrobial catheter, the method comprising the steps of:
 (a) comminuting an antimicrobial metal compound to a particle size of up to about 30 microns in diameter;
 (b) suspending the comminuted antimicrobial metal compound in a curable suspending agent selected from the group consisting of silicone, polyurethane and tetrafluoroethylene;
 (c) selecting a catheter from the group consisting of latex and silicone catheters;
 (d) coating the selected catheter with the suspending agent; and
 (e) curing the coating of suspending agent to form a layer of the cured suspending agent containing the comminuted antimicrobial metal compound bonded to the surface of the catheter.

15. A method as recited in claim 14 wherein the antimicrobial metal compound is selected from the group consisting of compounds of silver, gold and copper.

16. A method as recited in claim 15 wherein the antimicrobial metal compound comprises silver oxide.

17. A method as recited in claim 14 wherein the suspending agent comprises silicone and the catheter comprises a latex catheter.

18. A method as recited in claim 17 wherein the antimicrobial metal compound comprises silver oxide.

19. A method as recited in claim 14 further comprising the step of leaching the selected catheter with a leaching agent for removing undesirable compounds from the catheter prior to coating the catheter with the suspending agent.

20. A method as recited in claim 14 further comprising the step of preparing the surface of the catheter by contacting the surface with a bridging compound which is compatible with the material of the catheter and the suspending agent for bonding the suspending agent to the catheter.

21. A method as recited in claim 20 wherein the catheter comprises a latex catheter, the suspending agent comprises silicone and the bridging compound comprises mercaptopropyl trimethoxysilane.

22. A method as recited in claim 20 further comprising coating the catheter with an intermediate coating of the suspending agent after preparing the surface with the bridging compound.

23. A method as recited in claim 14 wherein the coating comprises a coating having a thickness of about 1 to about 15 microns in thickness.

24. A method as recited in claim 14 wherein the coating comprises about 0.2 milligrams to about 50 milligrams silver.

25. A method for the production of an antimicrobial catheter, the method comprising the steps of:
 (a) selecting a catheter from the group consisting of latex and silicone catheters;
 (b) comminuting an antimicrobial metal compound to a particle size of up to about 30 microns in diameter;
 (c) suspending the comminuted antimicrobial metal compound in a curable suspending agent;
 (d) leaching the selected catheter for removing any antioxidants, catalysts and other undesirable compounds which can be present in the catheter as a result of the process for forming the catheter;
 (e) preparing the surface of the selected catheter with a bridging compound by reacting the bridging compound with the catheter;
 (f) coating the catheter with the suspending agent containing the comminuted antimicrobial metal compound; and
 (g) curing the suspending agent to form a layer of the cured suspending agent containing the comminuted antimicrobial metal compound bonded to the surface of the catheter.

26. A method as recited in claim 25 wherein the antimicrobial metal compound comprises silver oxide.

27. A method as recited in claim 25 wherein the suspending agent is selected from the group consisting of silicone, polyurethane and tetrafluoroethylene.

28. A method as recited in claim 27 wherein the suspending agent comprises silicone.

29. A method as recited in claim 25 wherein the catheter comprises a latex catheter, the suspending agent comprises silicone and the surface of the catheter is prepared by reacting with mercaptopropyl trimethoxysilane.

30. A method as recited in claim 25 wherein the selected catheter is solvent leached with a ternary azeotropic mixture comprising toluene, isopropyl alcohol and water.

31. A method as recited in claim 25 further comprising coating the catheter with an intermediate coating of the suspending agent after preparing the surface with the bridging compound.

32. A method for forming a urological catheter having antimicrobial activity for inhibiting microbial migration along the catheter, the method comprising the steps of:
(a) forming a latex urological catheter;
(b) leaching the latex catheter with a leaching solution comprising a ternary azeotropic mixture of toluene, isopropyl alcohol and water for removing antioxidants and catalysts which can be present in the latex catheter as a result of the forming of the latex catheter;
(c) preparing the surface of the latex catheter by coating the surface with mercaptopropyl trimethoxsilane;
(d) comminuting silver oxide to a particle size of up to about 30 microns in diameter;
(e) suspending the comminuted silver oxide in a room temperature vulcanizable silicone;
(f) coating the surface of the latex catheter with the suspension containing the comminuted silver oxide; and
(g) curing the coating of suspending agent to form a layer of the cured suspending agent containing the comminuted silver oxide bonded to the surface of the latex catheter for forming a latex catheter having an antimicrobial surface.

33. A method as recited in claim 32 wherein the coating of cured suspending agent on the surface of the catheter comprises about 0.2 milligrams to about 50 milligrams silver oxide.

34. A method as recited in claim 32 further comprising coating the catheter with an intermediate coating of the suspending agent after preparing the surface with the bridging compound.

35. A method as recited in claim 32 further comprising the step of treating the coated catheter with a solvent for the cured suspending agent for exposing at least a portion of the antimicrobial metal compound in the coating.

36. A method as recited in claim 32 wherein the suspending agent and the solvent is selected the group consisting of potassium hydroxide, hydrogen peroxide and methyl ethyl ketone.

37. A method for the production of an antimicrobial catheter, the method comprising the steps of:
selecting a catheter from the group consisting of silicone catheters and latex catheters to be coated with an antimicrobial coating;
comminuting an antimicrobial metal compound to a particle size of up to about 30 microns in diameter;
suspending the comminuted antimicrobial metal compound in a curable suspending agent capable of bonding to the surface of the catheter;
coating the catheter with the suspending agent containing suspended antimicrobial metal compound; and
curing the suspending agent to bond the suspending agent containng antimicrobial metal compound to the surface of the catheter and to form an antimicrobial catheter having a fixed antimicrobial metal compound.

38. A method as recited in claim 25 further comprising the step of coating the prepared surface of the catheter on which the bridging agent is coated with a layer of suspending agent prior to coating the catheter with the suspending agent containing the comminuted antimicrobial metal compound.

* * * * *